United States Patent

McKay

[11] Patent Number: 6,146,420
[45] Date of Patent: Nov. 14, 2000

[54] OSTEOGENIC FUSION DEVICE

[75] Inventor: William F. McKay, Memphis, Tenn.

[73] Assignee: SDGI Holdings, Inc., Memphis, Tenn.

[21] Appl. No.: 08/988,142

[22] Filed: Dec. 10, 1997

[51] Int. Cl.$^7$ .................................................. A61F 2/44
[52] U.S. Cl. ............................................. 623/17; 606/61
[58] Field of Search .................... 623/16, 17; 606/61, 606/71–73

[56] References Cited

U.S. PATENT DOCUMENTS

| | | |
|---|---|---|
| 4,501,269 | 2/1985 | Bagby . |
| 4,863,476 | 9/1989 | Shepperd .................................. 623/17 |
| 4,878,915 | 11/1989 | Brantigan . |
| 4,961,740 | 10/1990 | Ray et al. . |
| 5,015,247 | 5/1991 | Michelson . |
| 5,336,223 | 8/1994 | Rogers ...................................... 623/17 |
| 5,390,683 | 2/1995 | Pisharodi ................................. 623/17 |
| 5,423,816 | 6/1995 | Lin ........................................... 623/17 |
| 5,645,598 | 7/1997 | Brosnahan, III ......................... 623/17 |
| 5,676,699 | 10/1997 | Gogolewski et al. ................... 623/16 |
| 5,766,253 | 6/1998 | Brosnahan, III ......................... 623/17 |

FOREIGN PATENT DOCUMENTS

| | | | |
|---|---|---|---|
| 577179 | 5/1994 | European Pat. Off. ................. | 623/17 |
| 94/07441 | 4/1994 | WIPO ..................................... | 623/17 |

*Primary Examiner*—Bruce Snow
*Attorney, Agent, or Firm*—Woodard, Emhardt, Naughton Moriarty & McNett

[57] ABSTRACT

An interbody osteogenic fusion device is provided that includes opposite end pieces with an integral central element. The end pieces are sized to maintain the height of an intervertebral disc space. The central element has a much smaller diameter so that the osteogenic fusion device forms an annular pocket around the central element. An osteogenic material is disposed within the annular pocket between the opposite end pieces. In one embodiment, the osteogenic material constitutes a collagen sheet soaked in a solution containing a bone morphogenetic protein. The osteogenic fusion device is configured so that the osteogenic material is in direct contact with the adjacent vertebral bone. In addition to the enhanced area of contact between the vertebral bone and the fusion material, the inventive osteogenic fusion device reduces stress-shielding and minimizes the radio-opacity of the implant so that growth of the fusion mass can be continuously assessed.

25 Claims, 4 Drawing Sheets

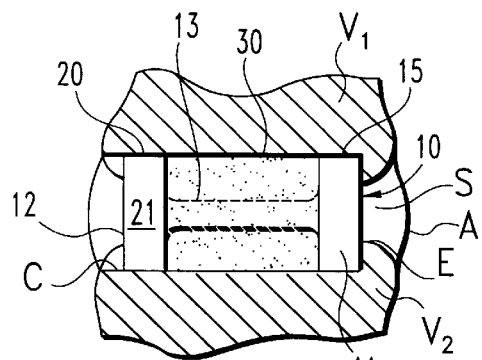
Fig. 9
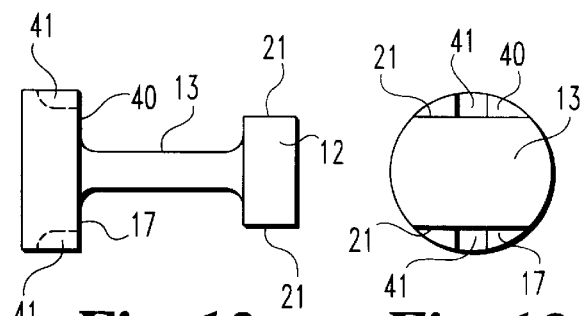
Fig. 12 Fig. 13
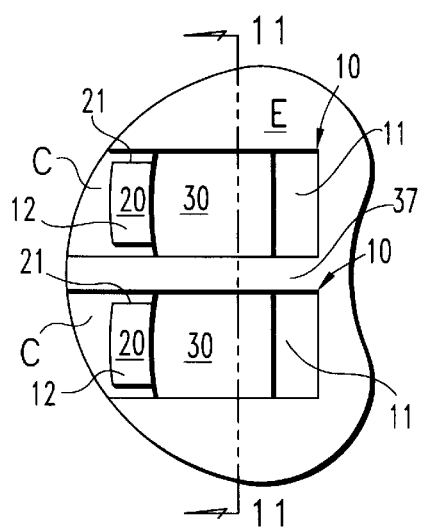
Fig. 10
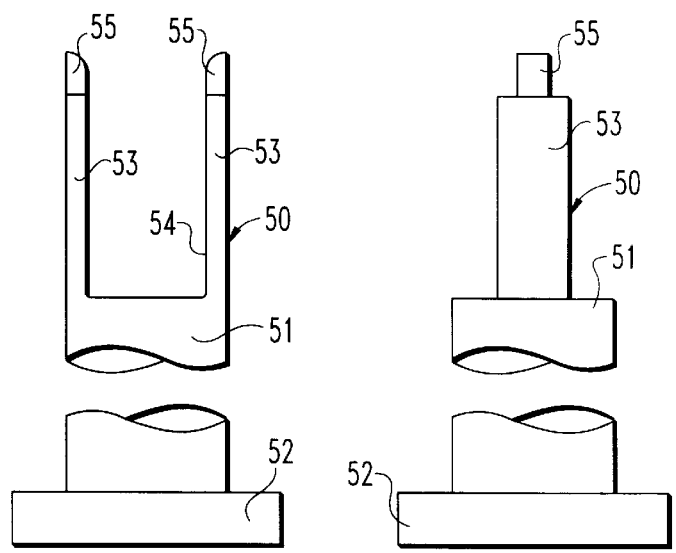
Fig. 14 Fig. 15
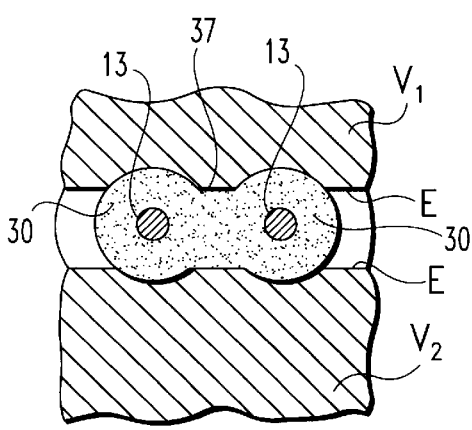
Fig. 11
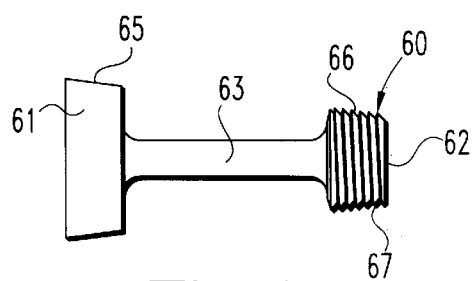
Fig. 16

OSTEOGENIC FUSION DEVICE

BACKGROUND OF THE INVENTION

The present invention relates to an implant to be placed into the intervertebral space left after the removal of a damaged spinal disc. Specifically, the invention concerns an osteogenic fusion device that enhances arthrodesis or fusion between adjacent vertebrae while also maintaining the normal spinal anatomy at the instrumented vertebral level.

In many cases, low back pain originates from damages or defects in the spinal disc between adjacent vertebrae. The disc can be herniated or can be affected by a variety of degenerative conditions. In many cases, these pathologies affecting the spinal disc can disrupt its normal anatomical function of the disc. In some cases, this disruption is significant enough that surgical intervention is indicated.

In one such surgical treatment, the affected disc is essentially removed and the adjacent vertebrae are fused together. In this treatment, a discectomy procedure is conducted to remove the disc nucleus while retaining the annulus. Since the disc material has been removed, a body must be placed within the intervertebral space to prevent the space from collapsing.

In early spinal fusion techniques, bone material, or bone osteogenic fusion devices, were simply disposed between adjacent vertebrae, typically at the posterior aspect of the vertebrae. In the early history of these osteogenic fusion devices, the osteogenic fusion devices were formed of cortical-cancellous bone which was not strong enough to support the weight of the spinal column at the instrumented level. Consequently, the spine was stabilized by way of a plate or a rod spanning the affected vertebrae. With this technique, once fusion occurred across and incorporating the bone osteogenic fusion device, the hardware used to maintain the stability of the spine became superfluous.

Following the successes of the early fusion techniques, focus was directed to modifying the device placed within the intervertebral space. Attention was then turned to implants, or interbody fusion devices, that could be interposed between the adjacent vertebrae, maintain the stability of the disc interspace, and still permit fusion or arthrodesis. These interbody fusion devices have taken many forms. For example, one prevalent form is a cylindrical hollow implant or "cage". The outer wall of the cage creates an interior space within the cylindrical implant that is filled with bone chips, for example, or other bone growth-inducing material. Implants of this type are represented by the patents to Bagby, U.S. Pat. No. 4,501,269; Brantigan, U.S. Pat. No. 4,878,915; Ray, U.S. Pat. No. 4,961,740; and Michelson, U.S. Pat. No. 5,015,247. In some cases, the cylindrical implants included a threaded exterior to permit threaded insertion into a tapped bore formed in the adjacent vertebrae. Alternatively, some fusion implants have been designed to be impacted into the intradiscal space.

Experience over the last several years with these interbody fusion devices has demonstrated the efficacy of these implants in yielding a solid fusion. Variations in the design of the implants have accounted for improvements in stabilizing the motion segment while fusion occurs. Nevertheless, some of the interbody fusion devices still have difficulty in achieving a complete fusion, at least without the aid of some additional stabilizing device, such as a rod or plate. Moreover, some of the devices are not structurally strong enough to support the heavy loads and bending moments applied at certain levels of the spine, namely those in the lumbar spine.

Even with devices that do not have these difficulties, other less desirable characteristics exist. Recent studies have suggested that the interbody fusion implant devices, or cages as they are frequently called, lead to stress-shielding of the bone within the cage. It is well known that bone growth is enhanced by stressing or loading the bone material. The stress-shielding phenomenon relieves some or all of the load applied to the material to be fused, which can greatly increase the time for complete bone growth, or disturb the quality and density of the ultimately formed fusion mass. In some instances, stress-shielding can cause the bone chips or fusion mass contained within the fusion cage to resorb or evolve into fibrous tissue rather than into a bony fusion mass.

A further difficulty encountered with many fusion implants is that the material of the implant is not radiolucent. Most fusion cages are formed of metal, such as stainless steel, titanium or porous tantalum. The metal of the cage shows up prominently in any radiograph (x-ray) or CT scan. Since most fusion devices completely surround and contain the bone graft material housed within the cage, the developing fusion mass within the metal cage between the adjacent vertebrae cannot be seen under traditional radiographic visualizing techniques and only with the presence of image scatter with CT scans. Thus, the spinal surgeon does not have a means to determine the progress of the fusion, and in some cases cannot ascertain whether the fusion was complete and successful.

The field of spinal fusion can be benefited by an intervertebral fusion device that can support bone growth material within the intervertebral space, while still maintaining the normal height of the disc space. The device would beneficially eliminate the risk of stress-shielding the fusion mass, and would also provide for visualization of the fusion mass as the arthrodesis progresses.

SUMMARY OF INVENTION

To address the current needs with respect to interbody fusion devices, the present invention contemplates a osteogenic fusion device that is configured to place as much of the bone growth inducing material as possible into direct contact with the adjacent bone. In one embodiment, the osteogenic fusion device includes an elongated body having opposite first and second end pieces separated by an integral central element. The central element has a significantly smaller diameter than the two end pieces. The osteogenic fusion device thus forms an annular pocket between the end pieces and around the central element.

In accordance with one aspect of the present invention, a bone growth inducing material is disposed within the annular pocket around the central element of the osteogenic fusion device. In one specific embodiment, the bone growth inducing material can constitute a sheet of a pharmaceutically suitable carrier for a bone growth factor, such as a bone morphogenetic protein. In this embodiment, the sheet can be a collagen sheet that is soaked with the BMP and then subsequently wrapped in spiral fashion around the central element of the osteogenic fusion device.

In one feature of the present invention, the osteogenic fusion device can be implanted in a bi-lateral approach. Specifically, two such osteogenic fusion devices can be inserted into prepared bores formed in the endplates of adjacent vertebrae after completion of a discectomy. The spinal loads are borne by the two end pieces that are in direct contact with the adjacent vertebral bodies. Preferably, the osteogenic fusion device has a length sufficient to allow the end pieces to at least partially contact the harder bone at the apophysis of the adjacent vertebrae. With the osteogenic fusion device thus inserted, the bone growth inducing material is in direct contact with the adjacent vertebral bodies. In addition, bone growth inducing material can be placed within the bi-lateral space separating the two osteogenic fusion devices. When fusion occurs, a substantial fusion mass is produced that is virtually uninterrupted by the material of the osteogenic fusion device itself.

Several alternative embodiments of the osteogenic fusion device are presented, all retaining the capability of supporting bone growth inducing material so that it is in direct contact with the adjacent vertebrae. In some embodiments, additional elements of the central element are provided, while in another embodiment, an intermediate piece is provided for further support across the disc space.

The present invention also contemplates an insertion tool and certain modifications to the osteogenic fusion device to accommodate the tool. In one preferred embodiment, the tool is essentially an elongated shank having opposite prongs extending therefrom. The prongs can engage truncated side walls of one of the end pieces. In addition, the opposite end piece can be formed with notches to receive the tips of the two prongs. With this design, the osteogenic fusion device can be a push-in or a threaded type osteogenic fusion device.

It is one object of the present invention to provide an interbody fusion device that allows the greatest possible contact between the adjacent vertebrae and the bone growth inducing material supported by the osteogenic fusion device. It is a further object to provide such a osteogenic fusion device that is capable of supporting the loads generated throughout the spine without stress-shielding developing bone within the osteogenic fusion device.

Another object of the invention is achieved by features that minimize the radio-opacity of the device. This results in a benefit to the surgeon of being able to more readily assess the progress of a spinal fusion.

Other objects and benefits of the present invention can be discerned from the following written description and accompanying figures.

DESCRIPTION OF THE FIGURES

FIG. 9 is a side, partially cross-sectional view of an intervertebral disc space with a osteogenic fusion device according to FIG. 1 implanted between adjacent vertebrae.

FIG. 10 is a top elevational view of the superior aspect of the instrumented vertebral level shown in FIG. 9, depicting bilateral placement of osteogenic fusion devices according to the present invention.

FIG. 11 is a cross-sectional view of the instrumented vertebral segment shown in FIG. 10, taken along line 10—10 as viewed in the direction of the arrows.

FIG. 12 is a top elevational view of a osteogenic fusion device, such as shown in FIG. 1, with features to permit insertion of the osteogenic fusion device.

FIG. 13 is an end elevational view of the osteogenic fusion device shown in FIG. 12.

FIG. 14 is a side elevational view of an insertion tool according to one embodiment of the present invention.

FIG. 15 is a top elevational view of the insertion tool shown in FIG. 14.

FIG. 16 is a top elevational view of a osteogenic fusion device for restoring the lordotic angle between adjacent vertebrae according to a further embodiment of the present invention.

DESCRIPTION OF THE PREFERRED EMBODIMENTS

Figure 1:
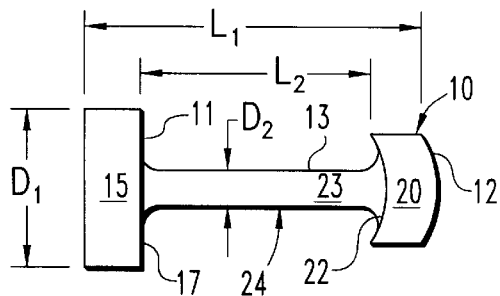
FIG. 1 is a top elevational view of a osteogenic fusion device in accordance with one embodiment of the present invention.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention contemplates osteogenic fusion devices for use as interbody fusion devices. The osteogenic fusion devices include opposite end pieces that are configured to span the intervertebral disc space and engage the adjacent vertebral bodies. The inventive osteogenic fusion devices include a central element separating the two end pieces and substantially spanning the anterior-posterior length of the disc space. The invention further contemplates that a bone growth-inducing material be disposed about the central element and between the opposite end pieces. When the inventive osteogenic fusion device is implanted within a patient, the bone growth-inducing material is in direct contact with the adjacent vertebral bodies. The end pieces are formed of a material sufficient to withstand the spinal loads generated at the instrumented vertebral level.

Figure 2:
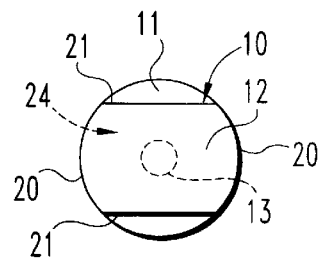
FIG. 2 is an end elevational view of one end of the osteogenic fusion device shown in FIG. 1.

In accordance with one embodiment of the invention, an osteogenic fusion device 10, depicted in FIGS. 1–2, includes a first end piece 11 and a second end piece 12. The end pieces are separated by a central element 13. The first end piece 11 could be substantially cylindrical or any geometrical shape and includes an outer bone contacting surface 15. The end piece 11 also defines an inwardly facing retaining surface 17. The central element 13 integrally extends from the retaining surface 17 of the first end piece 11.

The second end piece 12 also defines a bone contacting surface 20 that, in this embodiment, does not extend entirely around the end piece. The bone contacting surface 20 could be any geometrical shape, preferably circular and is defined at a radius equal to the radius of the outer surface 15 of the first end piece. Thus, as depicted in FIG. 2, the bone contacting surface 20 of the second end piece 12 is generally coincident with portions of the outer surface 15 of the first end piece 11 when the osteogenic fusion device is viewed along the longitudinal axis of its central element 13. The second end piece 12 also includes opposite truncated surfaces 21 that are disposed between the circular bone contacting surfaces 20. Preferably, the truncated surfaces 21 are generally flat and can be configured to be engaged by an insertion tool. The insertion tool preferably has arms that contact the flat truncated surfaces 21, yet still fall within the envelope defined by the outer surface 15 of the first end piece 11.

The second end piece 12 also defines a second retaining surface 22 that faces the first retaining surface 17 of the first end piece 11. Again, the central element 13 is preferably integral with and projects outwardly from the second retaining surface 22. Alternatively, the central element can be in the form of a central rod that is engaged within colinear bores formed in the two end pieces. In this variation, the engagement between the central rod and the end pieces can be threaded.

The central element 13 includes an outer central surface 23. Preferably, the central element 13 is substantially cylindrical along its length. In one aspect of the invention, the first end piece 11 defines a diameter $D_1$, while the central element 13 defines a diameter $D_2$. The diameter $D_1$ is at least equal to the height of the intervertebral space within which the osteogenic fusion device 10 is to be interposed. Most preferably, the diameter $D_1$ corresponds to the diameter of a cylindrical channel cut into the endplates of the adjacent vertebrae. In this instance, the diameter $D_1$ will be somewhat larger than the intervertebral disc space height. Moreover, the diameter $D_1$ is significantly larger than the diameter $D_2$ of the central element 13. This diameter differential creates an annular pocket 24 surrounding the central element 13.

The osteogenic fusion device 10 has a length $L_1$ between the opposite ends of the osteogenic fusion device. This length $L_1$ is preferably selected to be slightly less than the anterior-posterior length of the intervertebral disc space, although the length can be calibrated to the lateral dimension of the space. Most preferably, the length $L_1$ is sized so that the first and second end pieces 11, 12 can contact at least a portion of the apophysis or harder cortical bone at the perimeter of the vertebral endplates. The osteogenic fusion device 10 further defines a length $L_2$ which is essentially the length of the central element 13. The length $L_2$ is calibrated so that the end pieces 11 and 12 are sufficiently wide to provide adequate support between the adjacent vertebrae. Conversely, the length $L_2$ is sufficiently long so that the annular pocket 24 has the capacity for retaining a substantial quantity of bone growth-inducing material.

Figure 3:
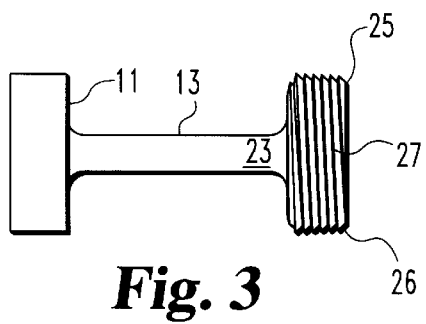
FIG. 3 is a top elevational view of an alternative embodiment of the osteogenic fusion device utilizing exterior threads.

In a modification of the osteogenic fusion device 10, the second end piece can be configured with threads. For example, as depicted in FIG. 3 an end piece 25 includes external bone engaging threads 26 extending from the outer surface 27. In accordance with this embodiment, the second end piece 25 can be cylindrical, like the first end piece 11, or the threads can be formed between truncated surfaces, such as truncated surfaces 21 in the prior embodiment. At any rate, the threaded end piece 25 is configured to be threadedly advanced into a drilled and tapped channel within the adjacent vertebral bodies. The first end piece 11 can also be threaded to facilitate insertion and to reduce the chance of expulsion.

In a further aspect of the invention, a bone growth inducing material 30 is provided for support by the osteogenic fusion device 10. Preferably the material 30 is in the form of a sheet. In a specific example, the carrier sheet 30 can be a collagen sheet that is soaked with a solution containing a bone growth inducing substance, or a bone morphogenetic protein (BMP). In accordance with the invention, the carrier sheet 30 can be formed of a variety of materials other than collagen, provided the materials are capable of containing a therapeutically effective quantity of a bone growth inducing substance or BMP. Moreover, the material 30, whether in sheet form or not, is most preferably susceptible to manipulation to be disposed within the annular pocket 24 of the fusion device 10.

Figure 5:
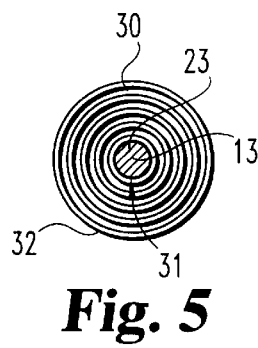
FIG. 5 is an cross-sectional view of the osteogenic fusion device and bone growth material shown in FIG. 4 taken along line 5—5 as viewed in the direction of the arrows.

In accordance with the specific embodiment, the carrier sheet 30 is wound around the outer surface 23 of the central element 13 (see FIG. 5). The carrier sheet 30 is held between the retaining surface 17 of the first end piece 11 and the retaining surface 22 of the second end piece 12. In accordance with one specific embodiment, the retaining surface 22 is curved or convex. In this way, the carrier sheet 30 can project into the convexity to serve as a sort of anchor to hold the carrier sheet 30 within the annular pocket 24 of the osteogenic fusion device 10. In addition, the convex surface 22 conforms better with the anterior portion of the vertebral body profile when the fusion device is implanted.

Figure 6:
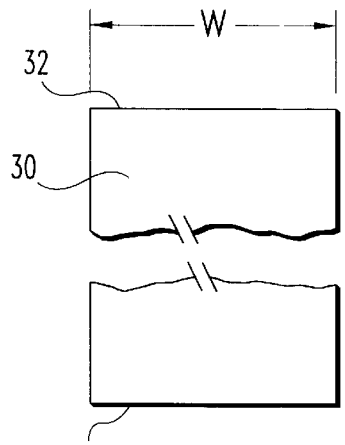
FIG. 6 is a plan view of a sheet for a bone growth inducing material used with the osteogenic fusion device shown in FIG. 4.

In the illustrated embodiment, the carrier sheet 30 can be provided as a single sheet, as shown in FIG. 6. The inner end 31 of the sheet is disposed against the central outer surface 23 of the central element 13. The sheet can be wound in a spiral fashion about the central element 13 until its outer end 32 is disposed adjacent the outer surface 15 of the first end piece 11. The carrier sheet 30 has width W that is preferably slightly larger than the length $L_2$ between the first and second end pieces to allow a portion of the carrier sheet 30 to project into the concave retaining surface 22 of the second end piece 12. The overall length of the sheet 30 between ends 31 and 32 depends upon its thickness and the difference in diameters $D_1$ and $D_2$. For example, in one embodiment the diameter $D_2$ is about one-fourth (¼) the diameter $D_1$.

Preferably, the length is sufficient so that the carrier sheet 30 can be tightly wound about the central element 13 and fill the annular pocket 24. One important object of the present invention is that the carrier sheet 30 or bone growth inducing material reside in direct contact with the adjacent vertebral bone. Consequently, the sheet 30 is preferably wound so that its outer end 32 is at least slightly outside the envelope of the outer surface 15 of the first end piece 11.

Figure 4:
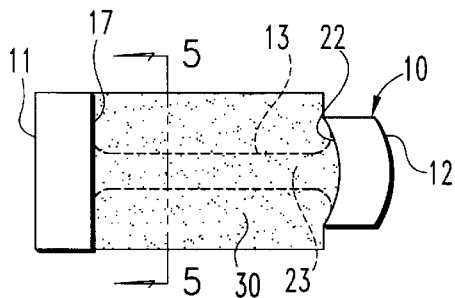
FIG. 4 is a top cross-sectional view of a osteogenic fusion device as shown in FIG. 1 with a bone growth inducing material supported by the osteogenic fusion device.

The carrier sheet 30 of FIGS. 4–6 illustrates one specific embodiment of bone growth-inducing material usable with the osteogenic fusion device of the present invention. It is also contemplated that the carrier can be in the form of a sponge, paste, gel or a settable osteogenic material. The osteogenic material must be provided in some form that can be generally retained about the central element 13 and within the annular pocket 24 of the osteogenic fusion device 10. Put differently, the present invention contemplates an osteogenic material that does not need to be contained in the traditional manner of the hollow cylindrical cages of the prior art. In these prior art devices, cancellous bone chips have been contained within a hollow cage. The present invention does not contemplate the use of bone chips alone. However, bone chips contained within a bone paste or a gel may be utilized with the osteogenic fusion device 10, provided that the paste or gel have a consistency sufficient to hold the bone growth inducing material on and within the osteogenic fusion device 10.

Figure 7:
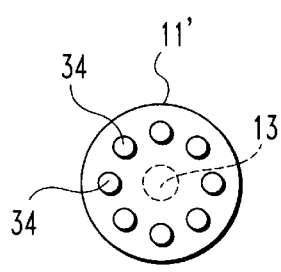
FIG. 7 is an end elevational view of one end of a osteogenic fusion device, such as the osteogenic fusion device of FIG. 1, modified to include apertures.
Figure 8:
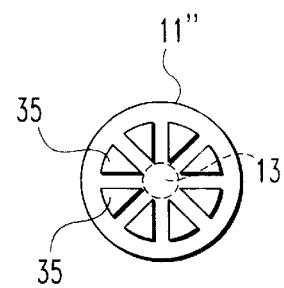
FIG. 8 is an end elevational view of one end of a osteogenic fusion device, such as the osteogenic fusion device of FIG. 1, modified to include apertures.

In accordance with one specific embodiment, the end pieces 11 and 12 are solid and circular in configuration. Alternative end piece configurations are shown in FIGS. 7 and 8. For example, end piece 11' can have a plurality of generally circular apertures 34 disposed circumferentially about the end piece, as shown in FIG. 7. The end piece 11" shown in FIG. 8 includes a plurality of pie-shaped apertures 35 so that the end piece gives the appearance of a spoked wheel. The second end piece 12 of the osteogenic fusion device 10 can have similar apertures defined therethrough. The apertures 34 and 35 in the end pieces 11', 11" provide a further avenue for facilitating fusion bone growth. The apertures themselves can be filled with a osteogenic material, such as a gel or a paste. Moreover, once the osteogenic fusion device 10 is implanted within an intervertebral disc space, osteogenic material can be packed around the osteogenic fusion device within the disc space. These additional apertures in the end pieces 11, 12 provide further avenues for the formation of a bony bridge between adjacent vertebrae.

The end pieces 11,12, etc. can also have non-circular shapes. For instance, the end pieces can be rectangular or other multi-sided shapes. If the osteogenic fusion device resides within a channel prepared in the endplates, the channel shape can be modified to conform to the bone engaging surfaces 15, 20 of the end pieces.

FIGS. 9–11 depict a pair of osteogenic fusion devices 10 implanted in a bi-lateral configuration between adjacent vertebral bodies $V_1$ and $V_2$. As depicted, the disc annulus A is retained but at least one portal must be defined in the annulus A to permit insertion of the osteogenic fusion devices 10. The present invention also contemplates insertion of each osteogenic fusion device 10 through its own portal formed in the disc annulus A. Alternatively, in conformance with other known procedures, a single portal can be provided through which each osteogenic fusion device 10 is successively inserted. Further in accordance with the present invention, the osteogenic fusion devices 10 can be positioned within the intervertebral disc space according to known posterior or postero-lateral techniques.

According to the present invention, the osteogenic fusion device 10 is inserted into the disc space S with the first end piece 11 proceeding first into the space. Preferably, a channel C is bored into the vertebral endplates E to a preferred depth of insertion of the osteogenic fusion device 10, in accordance with known techniques. If the osteogenic fusion device to be implanted is of the type shown in FIG. 3 with the threaded second end piece 25, the channels C can be appropriately drilled and tapped to accommodate the bone engaging threads 26. In a modification of this embodiment, the first end piece 11 can also carry external threads.

The preferred embodiment contemplates a generally cylindrical osteogenic fusion device placed within circular channels. Alternatively, the osteogenic fusion devices can operate as spacers that directly contact the endplates, without a prepared channel. In this instance, the bone engaging surfaces of the end pieces can be modified to conform to the vertebral endplate geometry.

As depicted in FIGS. 9–11, the osteogenic material 30 is disposed in direct contact with the adjacent vertebral endplates E. Moreover, the placement of osteogenic fusion devices 10 can present a medial space 37 between the two osteogenic fusion devices. Osteogenic material can then be placed within the medial space 37, again in direct contact with the osteogenic material 30 situated around the central elements 13 of each of the osteogenic fusion devices 10. Once complete fusion occurs, new bone growth will substitute the carrier material 30 to form a solid bony bridge spanning the adjacent vertebrae $V_1$, $V_2$. As can be seen from FIGS. 9–11, the region of continuous bone growth is very substantial and is not interrupted by the structure of the fusion device itself.

It is understood, of course, that the end pieces 11 and 12 provide sufficient support for the vertebral loads passing between the adjacent vertebrae. At the same time, this load bearing capacity is concentrated outside the middle regions of the vertebral endplates E. It is known that the central region of the endplates is very rich in blood flow and has a high capacity for new bone growth. Thus, the elimination of structural material of the osteogenic fusion device 10 from that region provides for a faster and more complete arthrodesis than may have been possible with prior fusion cages.

Referring next to FIGS. 14, 15, an insertion tool 50 is depicted for inserting a osteogenic fusion device 10 according to the present invention. The insertion tool 50 includes a solid shank 51 to which a knob or handle 52 is affixed. The knob 52 is configured for manual grasping and manipulation during insertion of the osteogenic fusion device. In the case where the osteogenic fusion device is not threaded, the insertion tool 50 simply acts as a pushing device. On the other hand, in the instance where the osteogenic fusion device includes threaded end pieces such as shown in FIG. 3, the insertion tool 50 must be rotated as the end piece is threaded into the prepared channel between the adjacent endplates.

The insertion tool 50 includes a pair of prongs 53 that are disposed apart to define an end piece recess 54. For insertion of the osteogenic fusion device 10 shown in FIG. 1, the end piece recess 54 is configured so that the prongs 53 are in tight contact with the truncated surfaces 21 of the second end piece 12. The outer surface of the prongs 53 can conform to a portion of the outer surface 15 of the first end piece 11.

The insertion tool 50 depicted in FIGS. 14–15 also includes tapered tips 55 at the ends of each of the prongs 53. These tapered tips are configured to be received within driving notches 41 in a modified first end piece 40, as depicted in FIGS. 12–13. The osteogenic fusion device depicted in FIGS. 12–13 is substantially similar to the osteogenic fusion device 10 shown in FIG. 1, with the exception of the added driving notches. The insertion tool 50 is configured so that the tips 55 project into the notches 41 while the prongs 53 directly contact the truncated surfaces 21 of the second end piece 12. This particular configuration of the insertion tool is particularly useful for threaded insertion of the osteogenic fusion device. Preferably, the prongs 53 have an effective outer diameter that is approximately equal to the diameter $D_1$. Moreover, the prongs 53 can have an arc segment configuration to complement the truncated surfaces 21. If the end piece 12 is threaded (see FIG. 3), the prongs 53 can include complementary threads along their length.

The present invention also contemplates a osteogenic fusion device for restoring the normal lordotic angle of an intervertebral segment. Specifically, a lordotic osteogenic fusion device 60 includes a first end piece 61 and a second end piece 62 as shown in FIG. 16. As with the prior embodiments, a central element 63 is provided to connect the two end pieces. The outer surface 65 of the first end piece 61 is in the form of a frusto-conical surface. The outer surface 65 tapers toward the second end piece 62 at a preferred lordotic angle. Similarly, the outer surface 66 of the second end piece 62 is also tapered at a similar lordotic angle. Alternatively, the second end piece 62 can include threads formed on the outer surface 66. While the threads 66 at the smaller second end piece 62 may not contact the vertebral endplates at the larger insertion end, the threads will contact the endplates at the anterior end of the intradiscal space and will act as an anchor to resist expulsion of the lordotic osteogenic fusion device 60.

Figure 17:
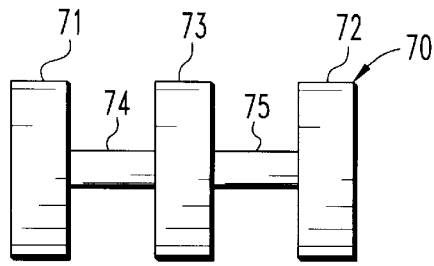
FIG. 17 is a top elevational view of a osteogenic fusion device according to a further embodiment of the present invention.

The present invention contemplates several modifications to the basic osteogenic fusion device 10. For example, the osteogenic fusion device 70 shown in FIG. 17 includes first and second end pieces 71, 72 and a center piece 73 disposed between the two end pieces. First and second central elements 74 and 75 connect each of the end pieces 71, 72 to the center piece 73. In this instance, the center piece 73 will contact the interior of the disc endplates E. Osteogenic material, such as carrier sheets 30, can be disposed or wound around each of the central elements 74, 75 until the end of the bone growth inducing material is exposed at the outer surface of the osteogenic fusion device 70.

Figure 18:
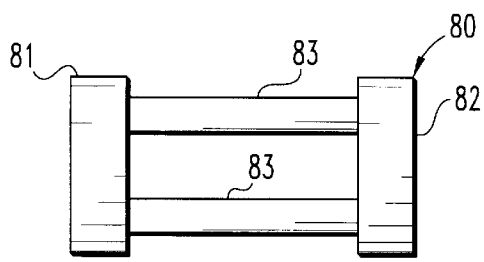
FIG. 18 is a top elevational view of a osteogenic fusion device according a still further embodiment of the present invention.
Figure 19:
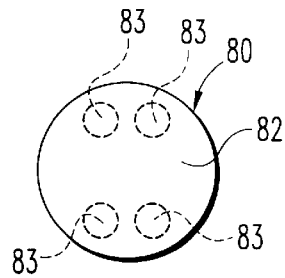
FIG. 19 is an end elevational view of the osteogenic fusion device shown in FIG. 18.

In a further modification, a osteogenic fusion device 80 depicted in FIG. 18 includes first and second end pieces 81 and 82 that are connected by a plurality of central beams 83. In the illustrated embodiment as shown in FIG. 19, four such beams 83 are provided; however, other arrangements and numbers of beams are contemplated. Important aspects of the present invention are retained by the osteogenic fusion device 80 because osteogenic material can be supported by the several beams 83 between the first and second end pieces 81, 82, with the bone growth inducing material in direct contact with the adjacent vertebral bodies.

Figure 20:
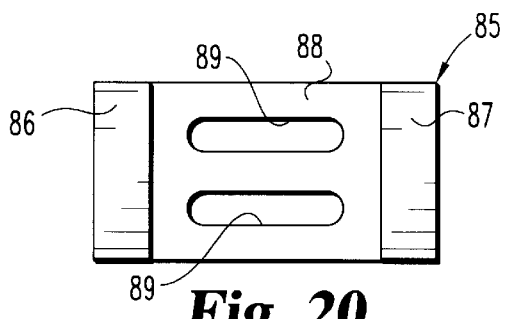
FIG. 20 is a top elevational view of a osteogenic fusion device according to another embodiment of the present invention.
Figure 21:
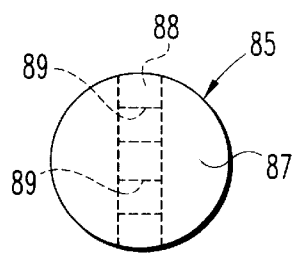
FIG. 21 is an end elevational view of the osteogenic fusion device shown in FIG. 20

The two embodiments of FIGS. 20–21 and FIGS. 22–23 pose a slight deviation from the general concept of the osteogenic fusion device 10. In these two embodiments, the smaller diameter central element 13 is replaced by a wall. In the embodiment of FIGS. 20–21, a osteogenic fusion device 85 includes first and second ends 86, 87 separated by a central element 88. The first and second ends 86 and 87 can be in the form of short cylindrical sections, such as the first end piece 11 of the osteogenic fusion device 10 in FIG. 1. While the central element 88 can be in the form of a solid wall, the osteogenic fusion device 85 preferably includes a number of slots 89 defined through the central element 88. In accordance with the specific embodiment, the slots extend along substantially the entire length of the central element 88. While the osteogenic fusion device 85 deviates somewhat from the concept of the osteogenic fusion device 10, this latter osteogenic fusion device 85 retains the broad beneficial feature of the present invention, namely provision for direct contact between osteogenic material supported by the osteogenic fusion device 85 and the vertebral endplates. In the present instance, the osteogenic material can be situated on opposite sides of the central element 88. In addition, the material can be passed through the slots 89.

Preferably, the osteogenic fusion device 85 will be oriented within the intervertebral disc space with the central element 88, or wall, spanning between the adjacent vertebrae. This central element 88, then, will provide additional structure and load bearing capability for sustaining the spinal loads at the instrumented level.

Figure 22:
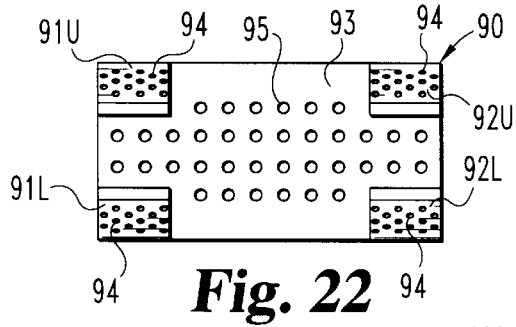
FIG. 22 is a top elevational view of a osteogenic fusion device according to yet another embodiment of the present invention.
Figure 23:
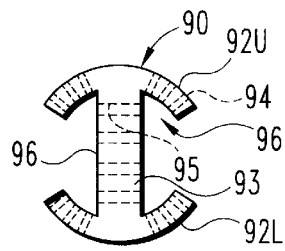
FIG. 23 is an end elevational view of the osteogenic fusion device shown in FIG. 22.

The osteogenic fusion device 90 of FIGS. 22–23 operates on a similar concept to the osteogenic fusion device 85. However, in this instance, the first and second end pieces are in the form of arc segments, rather than shortened cylinders. Specifically, the osteogenic fusion device 90 includes upper and lower first arc segments $91_U$ and $91_L$, and upper and lower second arc segments $92_U$ and $92_L$. The osteogenic fusion device 90 also includes a central element 93 that is again in the form of a wall connecting the first and second end pieces. As can be seen most clearly in FIG. 23, the arc segments 91, 92 and central element 93 define a pair of cavities 96 for containing osteogenic material. In this embodiment, the osteogenic material can be contained completely from end to end of the osteogenic fusion device 90. In the prior embodiments, the osteogenic material is contained within retaining surfaces of the opposite end pieces. In accordance with a specific embodiment, the osteogenic fusion device 90 includes a plurality of apertures 94 defined in each of the upper and lower first and second arc segments $91_U$, $91_L$, $92_U$ and $92_L$. Similarly, a plurality of apertures 95 can be defined through the central element 93. In this manner, the apertures provide the maximum capacity for bone ingrowth not only around, but also through the osteogenic fusion device 90.

Figure 24:
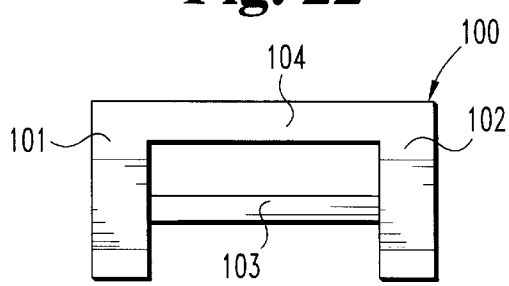
FIG. 24 is a top elevational view of a osteogenic fusion device according to a further embodiment of the present invention.
Figure 25:
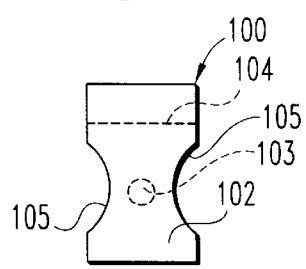
FIG. 25 is an end elevational view of the osteogenic fusion device shown in FIG. 24.
Figure 26:
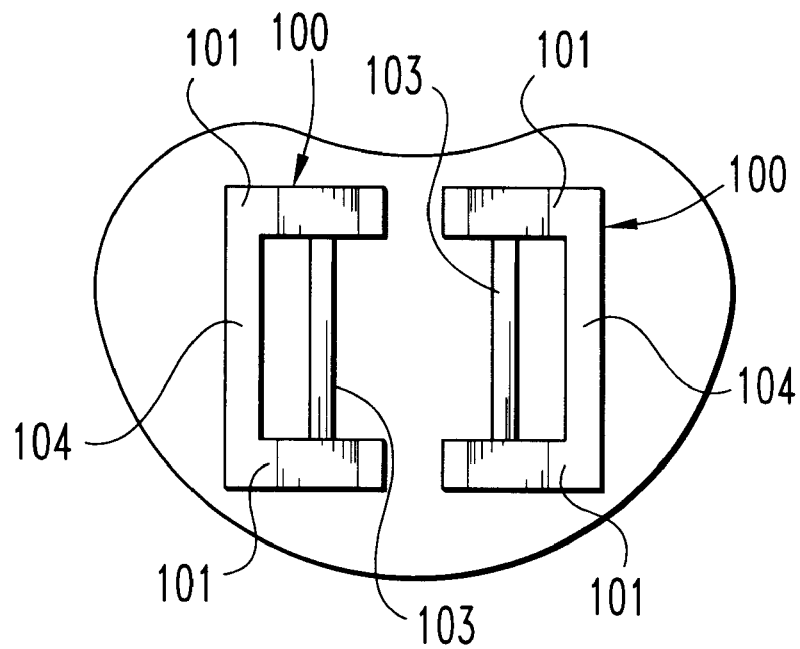
FIG. 26 is a top elevational view of a pair of fusion devices according to FIGS. 24–25 disposed in a bilateral configuration in the lumbar spine.
Figure 27:
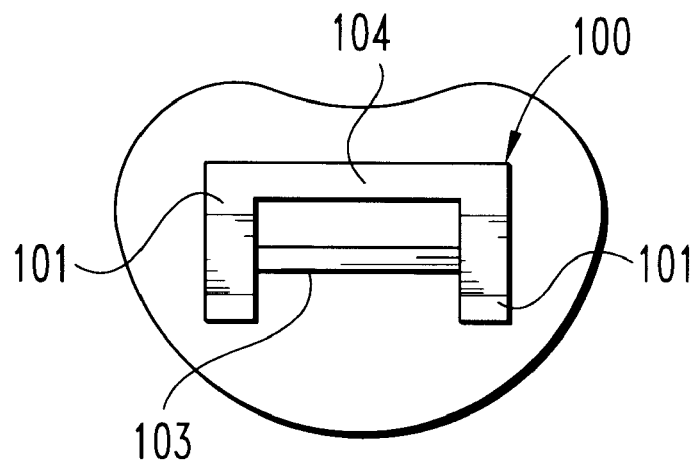
FIG. 27 is a top elevational view of a fusion device according to FIGS. 24–25 disposed in the cervical spine.

A osteogenic fusion device 100 shown in FIGS. 24–25 again presents a slightly different concept. This osteogenic fusion device 100 includes a first end plate 101, a second end plate 102 and a central element 103 that are similar to the like-named components of the osteogenic fusion device 10. However, the osteogenic fusion device 100 also includes a side piece 104 spanning between the first and second end pieces 101, 102. Moreover, unlike the osteogenic fusion device 10, the first and second end pieces 101, 102 are not generally circular in configuration, but are generally rectangular in configuration. In one specific embodiment, the end pieces 101, 102 can include cut outs 105 at opposite sides of the end pieces to provide further avenues for the formation of a bony bridge between adjacent vertebrae. As with the prior embodiments, the osteogenic fusion device 100 provides means for adequately containing osteogenic material, such as in the form of the carrier sheet 30. In this embodiment, the carrier sheet 30 can be wound around the central element 103, in the manner described above. This particular embodiment of the invention, namely osteogenic fusion device 100, is preferably adapted for use in the lumbar spine as illustrated in FIG. 26 and in the cervical spine illustrated in FIG. 27, and is consequently sized accordingly.

The present invention contemplates osteogenic fusion devices that are formed of a material that is sufficiently strong to support the adjacent vertebrae and to maintain the disc height of the instrumented intervertebral space. For example, the osteogenic fusion devices, such as osteogenic fusion device 10, can be formed of a biocompatible sterilizable metal, such as stainless steel or titanium. Of course, other medical grade materials are contemplated, such as certain ceramics, polymers, etc., as well as allograft and xenograft bone, provided the materials are sufficiently strong. The overall dimensions of each of the osteogenic fusion devices described above depends upon the instrumented level. For example, a osteogenic fusion device for use in the cervical spine must necessarily be smaller than a osteogenic fusion device used in the lumbar spine. Moreover, the relative dimensions of the components of the osteogenic fusion devices may be altered depending upon the vertebral level to be instrumented. For example, a osteogenic fusion device, such as osteogenic fusion device 10, for use in the lumbar spine, may require a central element 13 having a diameter $D_2$ that is more than one fourth of the outer diameter $D_1$ of the outer surface 15 of the first end piece 11. In some instances, the lumbar spine may generate bending moments across a osteogenic fusion device, such as osteogenic fusion device 10, that would require a stronger central element 13.

In accordance with the present invention, the illustrated osteogenic fusion devices can be of the push-in or threaded-in type. Of course, the end pieces, such as end pieces 11, 12 of osteogenic fusion device 10, can include various surface characteristics known in the art for enhancing the degree of fixation of the osteogenic fusion device between the adjacent vertebrae. For example, the end pieces can include certain macro surface features for penetrating the vertebral endplates to resist expulsion of the osteogenic fusion devices. Likewise, the surfaces, such as outer surface 15 and bone contacting surface 20 can be provided with bone ingrowth coatings so that a certain amount of bone ingrowth occurs even between the end pieces and the adjacent vertebral bodies.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An implant for promoting fusion bone growth in the space between upper and lower adjacent vertebrae, comprising:
   a load bearing member including opposite end pieces and a rigid elongated central element extending between said end pieces,
   said opposite end pieces each having two opposite surfaces configured to contact and support the upper and lower adjacent vertebrae, said opposite end pieces sized to maintain the space between the adjacent vertebrae,
   said central element being sized relative to said opposite end pieces to define a pocket between said central element and the adjacent vertebrae when the adjacent vertebrae are supported by said opposite end pieces, said pocket configured to contain an osteogenic material disposed about said central element and in intimate contact with the adjacent vertebrae when the vertebrae are supported by said opposite end pieces; and
   a biocompatible sheet carrier for an osteogenic material, said biocompatible sheet carrier wound around said central element within said pocket.

2. The implant for promoting fusion bone growth according to claim 1, wherein said opposite end pieces include:
   a first end piece having a first dimension between said two opposite surfaces, said first dimension being sized to maintain the space between the adjacent vertebrae; and
   a second end piece having a dimension between said two opposite surfaces substantially equal to said first dimension and a second dimension transverse to said dimension that is less then said first dimension.

3. The implant for promoting fusion bone growth according to claim 1, wherein each of said two opposite surfaces of each of said opposite end pieces is arcuate.

4. The implant for promoting fusion bone growth according to claim 3, wherein said opposite end pieces include:
   a substantially circular first end piece; and
   a second end piece with said two opposite surfaces being circular and including truncated non-circular sides between said two opposite surfaces.

5. The implant for promoting fusion bone growth according to claim 1, wherein:
   each of said opposite end pieces defines a first dimension between said two opposite surfaces; and
   said elongated central element defines a central dimension transverse to said longitudinal axis that is less than said first dimension.

6. The implant for promoting fusion bone growth according to claim 5, wherein said central dimension is no more than about 25% (twenty-five percent) of said first dimension.

7. The implant for promoting fusion bone growth according to claim 1, further comprising an osteogenic material contained within said pocket and arranged to contact the adjacent vertebrae when the vertebrae are supported by said opposite end pieces.

8. The implant for promoting fusion bone growth according to claim 7, wherein said osteogenic material includes an osteogenic substance disposed within said biocompatible sheet carrier.

9. The implant for promoting fusion bone growth according to claim 1, further comprising an osteogenic material contained within said pocket and arranged to contact the adjacent vertebrae when the vertebrae are supported by said opposite end pieces.

10. The implant for promoting fusion bone growth according to claim 8, wherein said osteogenic substance is a bone morphogenetic protein.

11. The implant for promoting fusion bone growth according to claim 1, wherein said two opposite surfaces of at least one of said end pieces includes threads.

12. The implant for promoting fusion bone growth according to claim 1, wherein each of said opposite end pieces defines a retaining surface connected to said central element, at least one retaining surface being concave.

13. The implant for promoting fusion bone growth according to claim 1, wherein at least one of said opposite end pieces includes a plurality of apertures defined therethrough in communication with said pocket.

14. The implant for promoting fusion bone growth according to claim 1, wherein said central element is attached to said opposite end pieces substantially equidistant from each of said two opposite surfaces of each end piece.

15. The implant for promoting fusion bone growth according to claim 1, wherein said load bearing member includes a center piece having two opposite surfaces configured to contact the adjacent vertebrae, said center piece being connected to said central element between said opposite end pieces and bisecting said pocket.

16. The implant for promoting fusion bone growth according to claim 1, wherein said central element is attached to said opposite end pieces substantially equidistant from each of said two opposite surfaces of each end piece.

17. The implant for promoting fusion bone growth according to claim 1, further comprising a side piece spanning between said opposite end pieces and offset from said central element.

18. The implant for promoting fusion bone growth according to claim 1, wherein said central element includes at least two rods connected to said opposite end pieces.

19. The implant for promoting fusion bone growth according to claim 1, wherein said central element includes a wall connected to said opposite end pieces, said wall bifurcating said pocket.

20. The implant for promoting fusion bone growth according to claim 19, wherein said wall includes at least one opening defined therethrough and communicating with said pocket.

21. The implant for promoting fusion bone growth according to claim 20, wherein said at least one opening is an elongated slot.

22. The implant for promoting fusion bone growth according to claim 1, wherein at least one of said opposite end pieces includes opposite arc segments, said arc segments defining said two opposite surfaces contacting the adjacent vertebrae.

23. The implant for promoting fusion bone growth according to claim 22, wherein said opposite arc segments include a plurality of apertures defined therethrough communicating with the adjacent vertebrae when said two opposite surfaces are in contact with the adjacent vertebrae.

24. The implant for promoting fusion bone growth according to claim 1, wherein said elongated central element has a length between said opposite end pieces, said length being sized to maintain contact between said opposite end pieces and cortical bone of the adjacent vertebrae when said load bearing member is in contact with the adjacent vertebrae.

25. An implant for promoting fusion bone growth in the space between upper and lower adjacent vertebrae, comprising:

a load bearing member including opposite end pieces and a rigid elongated central element extending between said end pieces, said opposite end pieces each having two opposite surfaces configured to contact and support the upper and lower adjacent vertebrae, said opposite end pieces sized to maintain the space between the adjacent vertebrae, said opposite end pieces each defining a retaining surface connected to said central element, at least one retaining surface being concave, said central element being sized relative to said opposite end pieces to define a pocket between said central element and the adjacent vertebrae when the adjacent vertebrae are supported by said opposite end pieces, said pocket configured to contain an osteogenic material disposed about said central element and in intimate contact with the adjacent vertebrae when the vertebrae are supported by said opposite end pieces.

* * * * *

UNITED STATES PATENT AND TRADEMARK OFFICE
CERTIFICATE OF CORRECTION

PATENT NO. : 6,146,420
DATED : November 14, 2000
INVENTOR(S) : William F. McKay

It is certified that error appears in the above-identified patent and that said Letters Patent is hereby corrected as shown below:

Column 12,
Lines 39-43, please delete all of claim 9 and insert
-- The implant for promoting fusion bone growth according to claim 8, wherein said biocompatible sheet carrier is a collagen sheet. --.
Lines 58-61, please delete all of claim 14 and insert
-- The implant for promoting fusion bone growth according to claim 1, wherein said two opposite surfaces of each of said opposite end pieces is tapered to conform to an anatomic angle between the adjacent vertebrae. --.

Signed and Sealed this

Seventeenth Day of August, 2004

JON W. DUDAS
*Acting Director of the United States Patent and Trademark Office*